United States Patent
Flohr et al.

(10) Patent No.: US 11,328,423 B2
(45) Date of Patent: May 10, 2022

(54) CHARACTERIZATION OF PLAQUE

(71) Applicant: Siemens Healthcare GmbH, Erlangen (DE)

(72) Inventors: Thomas Flohr, Uehlfeld (DE); Bernhard Schmidt, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 783 days.

(21) Appl. No.: 15/831,462

(22) Filed: Dec. 5, 2017

(65) Prior Publication Data

US 2018/0165811 A1 Jun. 14, 2018

(30) Foreign Application Priority Data

Dec. 12, 2016 (EP) .................................... 16203444

(51) Int. Cl.
- G06T 7/00 (2017.01)
- A61B 6/03 (2006.01)
- A61B 6/00 (2006.01)

(52) U.S. Cl.
CPC ............ *G06T 7/0016* (2013.01); *A61B 6/032* (2013.01); *A61B 6/482* (2013.01); *A61B 6/504* (2013.01);

(Continued)

(58) Field of Classification Search
CPC ......... G06T 7/0016; G06T 2207/10081; G06T 2207/20081; G06T 2207/30104;

(Continued)

(56) References Cited

U.S. PATENT DOCUMENTS

| 9,220,419 | B2 | 12/2015 | Choi et al. | |
|---|---|---|---|---|
| 2007/0237288 | A1* | 10/2007 | Tkaczyk | A61B 6/032 378/5 |

(Continued)

FOREIGN PATENT DOCUMENTS

| CN | 101433464 A | 5/2009 |
|---|---|---|
| CN | 109009181 A | 12/2018 |
| JP | 2009178517 A | 8/2009 |

OTHER PUBLICATIONS

Boussel L. et al: "Photon counting spectral CT component analysis of coronary artery atherosclerotic plaque samples", British Journal of Radiology., Bd. 87, Nr. 1040, Aug. 1, 2014 (Aug. 1, 2014), pp. 20130798; XP055325294, GB; ISSN: 0007-1285, DOI: 10.1259/bjr.20130798; 2014.

(Continued)

*Primary Examiner* — Bo Joseph Peng

(74) *Attorney, Agent, or Firm* — Harness, Dickey & Pierce, P.L.C.

(57) ABSTRACT

A method is for the characterization of plaque in a region of interest inside an examination subject by way of a plurality of image data sets. The image data sets have been reconstructed from a plurality of projection data sets, which have been acquired via a CT device using different X-ray energy spectra. The method includes: acquiring the image data sets, which include a plurality of pixels. Spectral parameter values are acquired on a pixel by pixel basis using at least two image data sets. Character parameter values are then acquired on a pixel by pixel basis to characterize plaques on the basis of the spectral parameter values. An analysis unit and a computed tomography system are also disclosed.

26 Claims, 3 Drawing Sheets

(52) U.S. Cl.
CPC .......... *A61B 6/5217* (2013.01); *A61B 6/4241* (2013.01); *A61B 6/481* (2013.01); *A61B 6/486* (2013.01); *A61B 6/5235* (2013.01); *G06T 2207/10081* (2013.01); *G06T 2207/20081* (2013.01); *G06T 2207/30104* (2013.01)

(58) Field of Classification Search
CPC ....... A61B 6/482; A61B 6/5217; A61B 6/032; A61B 6/504; A61B 6/4241; A61B 6/481; A61B 6/486; A61B 6/5235; Y02A 90/10; G16H 50/30
See application file for complete search history.

(56) References Cited

U.S. PATENT DOCUMENTS

| | | | |
|---|---|---|---|
| 2008/0013672 A1* | 1/2008 | Krauss | G06T 7/0012 378/4 |
| 2009/0122953 A1 | 5/2009 | Imai | |
| 2010/0075373 A1* | 3/2010 | Hoyt | G06K 9/00147 435/40.5 |
| 2012/0207270 A1 | 8/2012 | Flohr et al. | |
| 2013/0129173 A1* | 5/2013 | Grbic | G06T 7/0012 382/131 |
| 2014/0050378 A1 | 2/2014 | Sengupta et al. | |
| 2015/0164342 A1 | 6/2015 | Choi et al. | |
| 2016/0321803 A1* | 11/2016 | Lamash | A61B 6/5205 |
| 2019/0282192 A1* | 9/2019 | Goshen | A61B 6/482 |

OTHER PUBLICATIONS

Obaid Daniel R., et.al.: "Dual-energy computed tomography imaging to determine atherosclerotic plaque composition: A prospective study with tissue validation", in: Journal of Cardiovascular Computed Tomography, 2014, vol. 8, pp. 230-237.
William Pavlicek et. al.: "Initial use of fast switched dual energy CT for coronary artery disease", SPIE—International Society for Optical Engineering. Proceedings, Bd. 7622, pp. 76221V, XP055372522, US ISSN: 0277-786X, DOI: 10.1117/12.844859; ISBN: 978-1-5106-0753-8; 2010.
German Office Action #16203444.1 dated May 24, 2017.
European Office Action dated Sep. 17, 2019.
Boussel, L et al:; "Photon counting spectral CT component analysis of coronary artery atherosclerotic plaque samples"; British Journal of Radiology; vol. 87; No. 1040, pp. 1-7; 2014.
Obaid, Daniel R. et al:; "Dual-energy computed tomography imaging to determine atherosclerotic plaque composition: A prospektive study with tissue validation"; Journal of Cardiovascular Computed Tomography; vol. 8; pp. 230-237; 2014.
Chinese Office Action and English translation thereof dated Nov. 20, 2020.
Second Office Action dated Apr. 30, 2021 in Chinese Application No. 2017113114019.

* cited by examiner

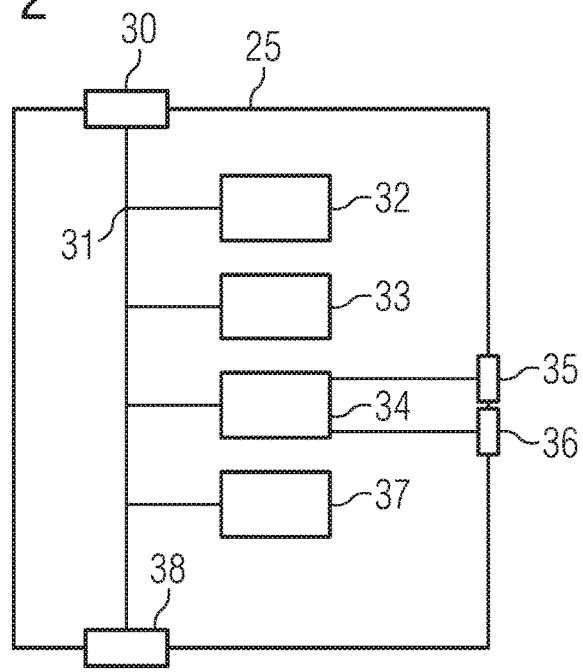
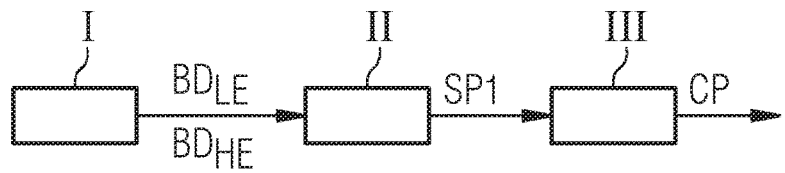
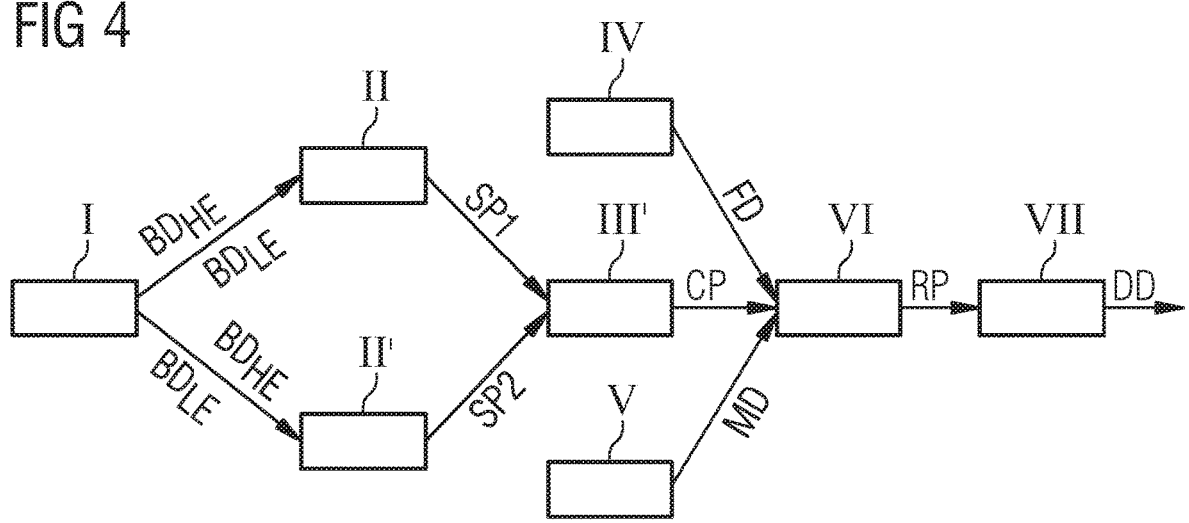

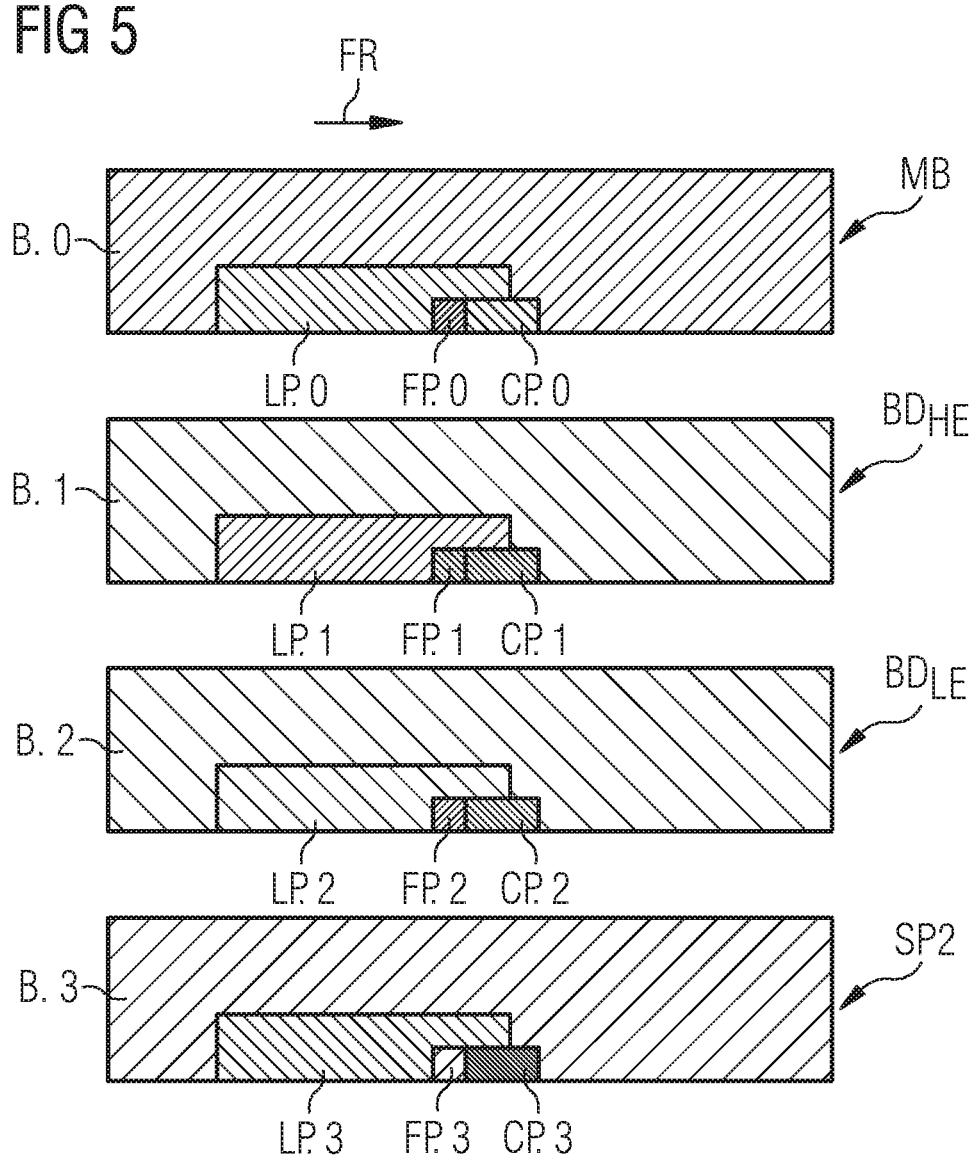

CHARACTERIZATION OF PLAQUE

PRIORITY STATEMENT

The present application hereby claims priority under 35 U.S.C. § 119 to European patent application number EP 16203444.1 filed Dec. 12, 2016, the entire contents of which are hereby incorporated herein by reference.

FIELD

At least one embodiment of the invention generally relates to a method for the characterization of plaque, an analytical apparatus, and/or also a computed tomography system.

BACKGROUND

Vascular diseases represent a growing challenge to medicine in the increasingly ageing population. Atherosclerosis is characterized, for example, by plaques in the blood vessels, in particular in the coronaries. If plaque becomes detached from the vascular walls, this is referred to as a "plaque rupture". If there is a plaque rupture in a coronary artery, this may lead to vascular occlusion and hence to a heart attack.

There are indications that the composition of the plaques and their morphology are factors that allow a statement to be made about the risk of the plaques and can thus serve to predict the likelihood of rupture. Lipid plaques for instance are rated as being particularly at risk of rupture; calcified plaques on the other hand are more likely to represent a stable final stage in coronary heart disease. The composition of plaques can thus serve as an indication for subsequent treatment. When particularly dangerous plaques are present, an aggressive therapy with statins, beta-blockers etc. can be introduced or the vessel can be supplied with a stent. In drug-based therapy, follow-up investigations of the plaques that are to be treated are indicated.

Until now, in order to characterize plaques, as a rule, methods such as intravascular ultrasound (IVUS), for example, in which an ultrasound probe is inserted into the vessel that is to be examined.

In contrast with these methods, computed tomography (CT) has until now tended to play only a subordinate role in the characterization of plaques. This is due first to the fact that the plaque composition was hitherto usually determined only on the basis of CT-values, that is, grayscale values (in Hounsfield units) of the pixels in a reconstructed slice image. Plaques with low CT-values in the region of fat are characterized as "lipid", plaques with average CT-values in the region of soft tissue as "fibrous", plaques with high CT-values as "calcified". In this simple analysis, an exact classification of a plaque is made more difficult by a considerable overlap of the CT value regions for the three aforementioned categories of plaque.

Second, the CT values are highly dependent on the tube voltage used for the scan. As a result thereof, the CT value regions for lipid, fibrous and calcified plaques derived from scans taken at the standard voltage of 120 kV cannot be transferred onto CT scans carried out at different tube voltages (for example, 80 kV or 100 kV). Here the tube voltages set a maximum energy of X-rays, which is why different X-ray spectra are also generated by way of different tube voltages are used. The tube voltage therefore often serves as the designation or characterization for a corresponding X-ray spectrum. Overall, however, the mere measurement of the CT value has a limited informative value for the characterization of the plaque composition.

SUMMARY

At least one embodiment of the present invention addresses the problem of providing a method for the characterization of plaque, an analytical device, and/or a computed tomography system, with which an improved characterization of plaque based on CT data is possible.

At least one embodiment of the present invention is directed to a method for the characterization of plaque; at least one embodiment of the present invention is directed to an analytical device; and at least one embodiment of the present invention is directed to a computed tomography system.

At least one embodiment of the present invention is directed to a method, used for the characterization of plaque in a region of interest inside an examination subject. The characterization is achieved by way of a plurality of image data sets that are reconstructed from a plurality of project data sets. The latter have been acquired via a CT device using different X-ray energy spectra in each case. The method comprises at least: acquiring the image data sets, which include a plurality of pixels; acquiring spectral parameter values on a pixel by pixel basis using at least two image data sets. On the basis of the spectral parameter values, character parameter values for characterizing the plaques are then acquired on a pixel by pixel basis.

At least one embodiment of the present invention is directed to a computed tomography system, including a CT device as well as an analytical device according to at least one embodiment of the invention.

Some of the components of the analytical device according to at least one embodiment of the invention can mainly be designed in the form of software components, and thus can be run by a processor and instructions in a memory. This applies in particular to the acquisition unit. Basically, this component can also partly be implemented in the form of software-supported hardware, for example, FPGAs or such like, in particular when particularly fast calculations are involved. Likewise, the required interfaces can be designed as software interfaces, if for example, it is merely a question of importing data from other software components. However, they can also be designed as hardware-based interfaces, which are activated by appropriate software.

A predominantly software-based design has the advantage that even computed tomography systems and/or evaluation computers that have already been used until now can be retrofitted in a simple manner with a software upgrade so that they operate in the manner according to at least one embodiment of the invention.

To this extent, at least one embodiment of the invention is further directed to a computer program product, comprising a computer program that can be loaded directly into a memory unit of a computed tomography system, with program segments to carry out all the steps in a method according to at least one embodiment of the invention, when the program is running in the computed tomography system. Such a computer program product can optionally include alongside the computer program additional components, such as, for example, documentation and/or additional components, also hardware components, such as for example, hardware keys (dongles etc.) for using the software.

For transportation to the computed tomography system and/or for storage on or in the computed tomography system, at least one embodiment of the invention is directed to a computer readable medium, for example, a memory stick, a hard disk or another transportable or fixedly installed data carrier, on which are stored the program segments of the computer program that are readable and executable by the computation unit in the computed tomography system. For this purpose, the computation unit can comprise, for example, one or a plurality of microprocessors working in combination or suchlike.

Further particularly advantageous variants and further developments of the invention will emerge from the claims and the description that follows, wherein the independent claims in one category of claim can also be further developed by analogy with the dependent claims and parts of the description in a different category of claim, and in particular, individual features of various embodiments or variants can also be combined to form new embodiments or variants.

BRIEF DESCRIPTION OF THE DRAWINGS

The invention is described hereinafter in greater detail with reference to the attached figures and by way of the embodiments. In the various figures, components that remain the same are denoted by identical reference signs. The figures are generally not to scale, in which:

FIG. 2 shows a schematic block circuit diagram of an embodiment of an analytical device according to the invention, FIG. 3 shows a block diagrammatic view of a simple embodiment of a method according to the invention, FIG. 4 shows a block diagrammatic view of a further embodiment of a method according to the invention and FIG. 5 shows four diagrammatic cross-section views through a blood vessel of a patient, which illustrate different steps in a method according to an embodiment of the invention.

DETAILED DESCRIPTION OF THE EXAMPLE EMBODIMENTS

Figure 1:
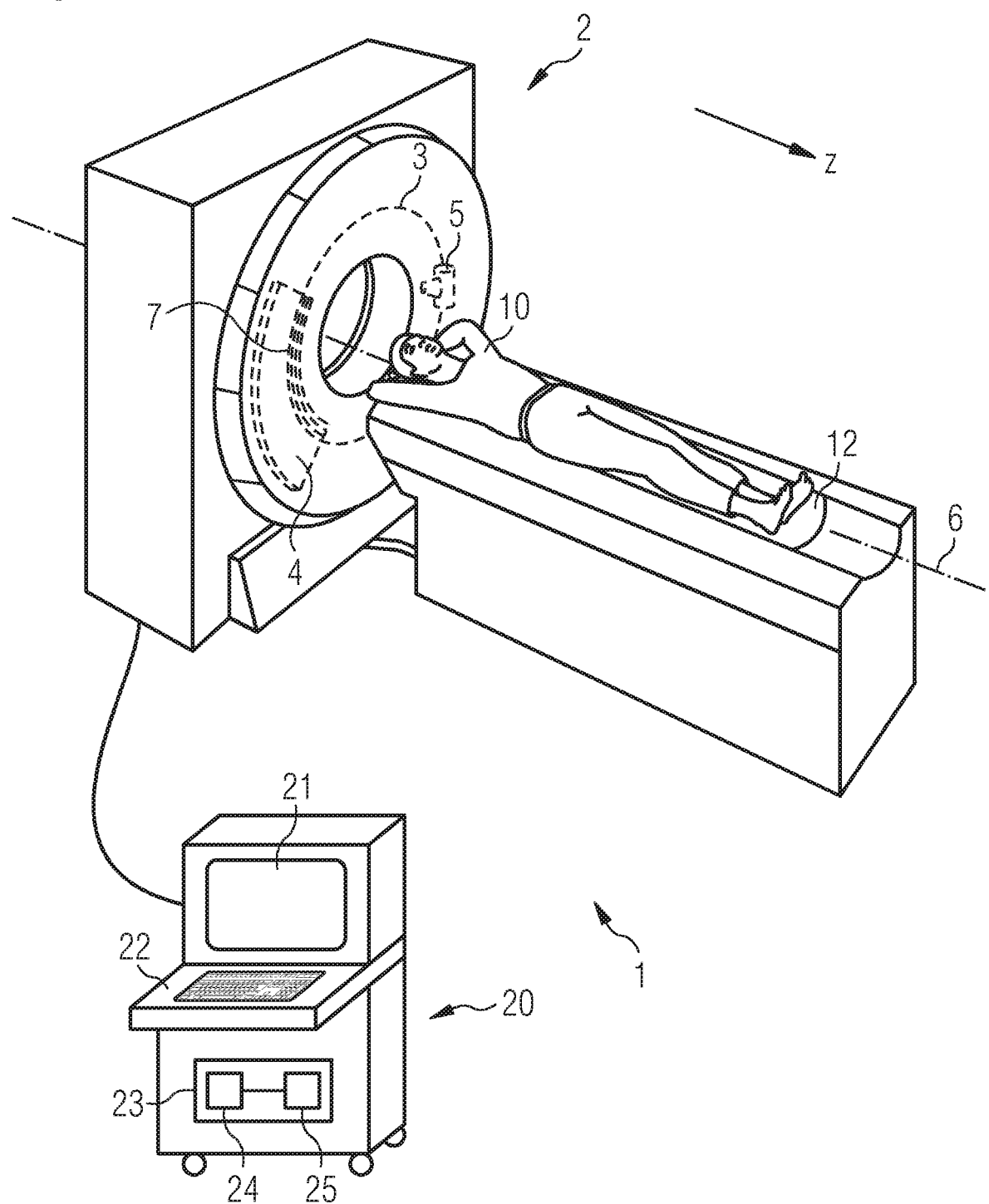
FIG. 1 shows a rough diagrammatic view of an embodiment of a computed tomography system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv)

source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a method, used for the characterization of plaque in a region of interest inside an examination subject. The characterization is achieved by way of a plurality of image data sets that are reconstructed from a plurality of project data sets. The latter have been acquired via a CT device using different X-ray energy spectra in each case. The method comprises at least: acquiring the image data sets, which include a plurality of pixels; acquiring spectral parameter values on a pixel by pixel basis using at least two image data sets. On the basis of the spectral parameter values, character parameter values for characterizing the plaques are then acquired on a pixel by pixel basis.

In the context of at least one embodiment of the invention, plaques are defined as chronically developing focal changes in the cells of the inner vascular wall and/or of the inner layers of the central vascular wall. As already stated in the introduction, plaques or atherosclerosis exist with different compositions and/or properties. These make it possible to distinguish or characterize the individual types of plaque, which allows classification into different classes or categories. The types of plaque can therefore be categorized, classified, or characterized as lipid, fibrous or calcified plaques. These categories correspond with the types of matter that give them their name based on the spectral parameter values. However, other—in particular both more and fewer—categories for the classification of the respective types of plaque are also possible.

For this purpose, a region of interest is examined, which preferably includes a blood vessel, that is, for example, a vein, an artery or in particular a coronary. This region is located inside an examination subject, which may be an animal, for example but is preferably a human, subject.

The data required for the characterization has been acquired using a CT device before the actual start of the method according to at least one embodiment of the invention. For this purpose, first a plurality of (that is at least more than one) projection data sets are acquired using different X-ray energy spectra in each case. Therefore, an X-ray energy spectrum is assigned to each projection data set. It includes values for local radiation intensities of the X-rays, which are detected in a detection element after passing through the examination subject, that is, they are detected in a pixel from a detector of the CT device.

The X-ray intensities are determined from a plurality of angles with respect to the examination subject. The X-ray energy spectra may differ between the projection data sets for example, in their maximum energy, their mean energy, their characteristic maximum radiation levels, that is, in their spectral distribution in general.

From the projection data sets, an equal number of image data sets is reconstructed by way of a known reconstruction method, such as, for example, filtered back projection, iterative reconstruction methods or suchlike. In the context of the invention, an image data set is defined as for example, a volume image or a slice image of the examination subject. The image data set includes a plurality of pixels which are usually referred to as voxels in the case of a three-dimensional volume data set and, in the case of a two-dimensional slice data set, as pixels.

In a first process step, the image data sets are acquired. This means that they can, for example, be taken directly from the aforementioned acquisition steps or reconstruction steps or stored in a memory, for example and be retrieved from it for the method according to at least one embodiment of the invention.

In a further step, spectral parameter values for at least one spectral parameter are acquired from the image data sets on a pixel by pixel basis. In this context, "on a pixel by pixel basis" means that the values are acquired pixel by pixel or voxel by voxel. The spectral parameter values thus represent in each pixel a combination of the image data from the image data sets with different X-ray energy spectra. For this purpose, where appropriate, after a registration of the data sets one onto the other, only two corresponding pixels in the image data sets can be combined. Alternatively, it is also possible for regions of pixels to be combined which are arranged in a region surrounding a central pixel, for which the spectral parameter value is to be determined.

Through this combination, the spectral parameter values contain spectral information on the respective pixel. Basically, the spectral parameter values can be determined from any number of image data sets with different spectra. In a simple and preferred variant of the method according to the invention, spectral parameter values are determined, however, from precisely two image data sets, that is, a low energy image data set and a high energy image data set. Here, not only values relating to a spectral parameter can be acquired, but it is also possible, however, to acquire values relating to a plurality of different spectral parameters that contain different spectral information, as is explained in more detail hereinafter.

On the basis of the spectral parameter values, character parameter values are subsequently acquired for the characterization of the plaques on a pixel by pixel basis. In the simplest scenario, the plaques can be characterized directly using the values acquired for a spectral parameter. For this purpose, for example, regions for spectral parameter values which assign a class or a category to the plaque in the respective pixel can be defined. It is also possible, however, to first combine values from different spectral parameters and then to carry out the characterization of the plaque on the basis of this combination, as is explained in more detail hereinafter.

Unlike the known prior art, the plaques are therefore characterized not only by their attenuation values, but also on the basis of the spectral parameter values. As described in the aforementioned, the latter contain detailed information on the properties of the plaque. As a result thereof, advantageously, a more precise characterization of the plaque on the basis of data that have been acquired using a CT device is possible.

For the characterization of plaque in a region of interest inside an examination subject, the analytical device referred to in the introduction includes an image data interface, an acquisition unit and a characterization unit. The analytical device is designed such that it carries out the steps in the method according to the invention for the characterization of plaque.

At least one embodiment of the present invention is directed to a computed tomography system, including a CT device as well as an analytical device according to at least one embodiment of the invention.

Some of the components of the analytical device according to at least one embodiment of the invention can mainly be designed in the form of software components, and thus can be run by a processor and instructions in a memory. This applies in particular to the acquisition unit. Basically, this component can also partly be implemented in the form of software-supported hardware, for example, FPGAs or such like, in particular when particularly fast calculations are involved. Likewise, the required interfaces can be designed as software interfaces, if for example, it is merely a question of importing data from other software components. However, they can also be designed as hardware-based interfaces, which are activated by appropriate software.

A predominantly software-based design has the advantage that even computed tomography systems and/or evaluation computers that have already been used until now can be retrofitted in a simple manner with a software upgrade so that they operate in the manner according to at least one embodiment of the invention.

To this extent, at least one embodiment of the invention is further directed to a computer program product, comprising a computer program that can be loaded directly into a memory unit of a computed tomography system, with program segments to carry out all the steps in a method according to at least one embodiment of the invention, when the program is running in the computed tomography system. Such a computer program product can optionally include alongside the computer program additional components, such as, for example, documentation and/or additional components, also hardware components, such as for example, hardware keys (dongles etc.) for using the software.

For transportation to the computed tomography system and/or for storage on or in the computed tomography system, at least one embodiment of the invention is directed to a computer readable medium, for example, a memory stick, a hard disk or another transportable or fixedly installed data carrier, on which are stored the program segments of the computer program that are readable and executable by the computation unit in the computed tomography system. For this purpose, the computation unit can comprise, for example, one or a plurality of microprocessors working in combination or suchlike.

Further particularly advantageous variants and further developments of the invention will emerge from the claims and the description that follows, wherein the independent claims in one category of claim can also be further developed by analogy with the dependent claims and parts of the description in a different category of claim, and in particular, individual features of various embodiments or variants can also be combined to form new embodiments or variants.

In principle, any complex methods can be used for the determination of the composition of matter on the basis of CT data. Thus, for example, dissection of basic matter is a demanding and computation-intensive method of acquiring as much information as possible about matter. This degree of detail is often not necessary for an adequate diagnosis. In contrast, it may be helpful to use a resource-saving, that is, less computation-intensive, method.

The acquisition of the spectral parameter values therefore preferably includes acquisition of a dual energy ratio. The dual energy ratio denotes in each pixel the ratio of the attenuation value of a low energy image data set to the attenuation value of a high energy image data set. Therefore, two image data sets are typically used, the low energy image data set having a lower maximum X-ray energy (for example, 80 KV) and the high image energy image data set having a higher maximum X-ray energy (for example, 140 KV).

Without restricting the scope of the invention, in at least one embodiment described in the description that follows, these two image data sets are used as a substitute for the plurality of image data sets. The dual energy ratio can therefore be calculated in each pixel via an arithmetic operation, that is, creation of a quotient from a corresponding pixel value in the low energy image data set and calculating a corresponding pixel value in the high energy image data set. If the dual energy ratio (DE-ratio) assumes values that are lower than a defined threshold, preferably lower than one (DE-ratio <1), as a result thereof, the plaque in the corresponding pixel can be characterized as lipid. Pixels with values for the dual energy ratio in a region of around one (DE-ratio ~1) should preferably be classified as fibrous, whereas plaque with dual energy ratio values greater than one (DE-ratio >1), is to be classified as calcified.

The dual energy ratio is usually a value that is irrespective of the concentration. This means that it characterizes the types of matter that occur irrespective of their local density. Nevertheless, it can be advantageous when characterizing plaque, to take the matter's concentration into account. The acquisition of the spectral parameter values therefore preferably includes acquisition of a dual-energy index. The dual-energy index is calculated for each pixel from the high energy image data set and the low energy image data set as follows:

$$\frac{BD_{LE}(x) - BD_{HE}(x)}{BD_{LE}(x) + BD_{HE}(x) + \alpha}$$

wherein $BD_{LE}(x)$ denotes a pixel value of the pixel x in the low energy image data set and $BD_{HE}(x)$ a pixel value of the pixel x in the high energy image data set BDHE. The parameter a is representation-dependent scaling factor. The dual-energy index contains according to its nature both information about the atomic composition (atomic number) of the matter and also about the matter concentration.

The subsequent characterization of plaque can therefore advantageously be acquired on the basis of the dual-energy index (DE-index). With dual-energy index values that are lower than zero (DE-index <0, particularly preferably DE-index <−0.05), the plaque is preferably characterized as lipid. In contrast, plaque with dual-energy index values that are greater than zero (DE-index >0, particularly preferably DE-index >0.05), is preferably classified as calcified. Plaque with dual-energy-index values in a region around (DE-index ~0, particularly preferably −0.05<DE-index <0.05) are preferably classified as fibrous.

It is, however, quite possible to use the dual energy index in addition to the dual energy ratio for the characterization of plaque. For this purpose, a combination parameter which combines the advantages of both parameters is particularly preferably determined from the two spectral parameters. Thus, for example, the combination parameter can be calculated using a weighted addition, which highlights as required the concentration dependence or the dependence on the composition of the matter.

In the method according to at least one embodiment of the invention, preferably in an additional step, risk parameter values are acquired on the basis of the character parameter values. Risk parameter values are understood here to mean values regarding the likelihood of a future pathogenesis. It therefore gives a prognosis for the likelihood for a possible further progression of the disease, such as, for example, the risk of a further accumulation of plaque or a plaque rupture. The risk parameter values can basically be determined only on the basis of the character parameter values, but further parameters can be taken into account, however, as is explained in closer detail hereinafter.

The acquisition of the risk parameter values is preferably achieved using morphological data. The morphological data can include values for a plaque volume, a plaque length, and a position of the plaque within the blood vessel or such like. The plaque volume can denote the entire volume of a plaque, but it can also describe the volumes of individual plaque regions, which have been characterized beforehand. The plaque length denotes the length of the plaque along a longitudinal length of the vessel or in the direction of the blood flow. From the plaque volume and the plaque length, a shape parameter of the plaque, which defines a ratio of the plaque length to a plaque thickness can be determined in addition, for example. From this, for example, conclusions can be drawn regarding the likelihood of plaque rupture.

The position of the plaque within the vessel, for example, ahead of branches, or such like, can therefore have considerable influences on the development of the plaque. In addition, the risk or the further development of the plaque can be influenced by what is known as "positive remodeling". This describes an expansion of the vessel that occurs as a reaction to plaque formation, whereby the vessel extends its cross section in order to retain its original lumen. Such a change can consequently have considerable influence on the further development of plaque and it therefore preferably taken into account in the acquisition of the risk parameter.

The acquisition of the risk parameter values is preferably achieved using blood flow data. The blood flow data preferably includes data from a previous CT perfusion examination, data from a measurement relating to the fractional flow reserve (FFR) and/or data relating to the fractional flow reserve, which was acquired via a CT device (CT-FFR). This data gives information on the local, that is, on the position of the plaque, the prevailing blood flow and can therefore advantageously contribute to determining the risk parameter values as precisely as possible. With the aid of blood flow data, any complex calculations can be carried out for risk analysis, such as for example, Finite-Element simulations (FEM), flow simulations or such like. First, as a result thereof, the prevalent shear forces can be determined and linked with the adhesive forces of the plaque, from which again risk parameter values can be determined, for example.

Secondly this data can also be taken into account in the context of a machine-learned characterization process, as described later in more detail.

On the basis of simultaneously and promptly acquired data, a characterization using character parameter values or a risk evaluation using the risk parameter values represents a snapshot without a chronological context. However, the acquisition of the risk parameter values preferably includes a chronological development of the character parameter values, the morphological data and/or the blood flow data.

The chronological development of the parameter values or data is preferably determined by way of two or more data acquisitions that are spaced chronologically apart. In order to determine the chronological development, the parameter values or data acquired at different points in time are compared. The comparison can take place on any level. This means that, for example, the spectral parameter values for different points of time can be compared with one another on a rudimentary evaluation level, registration of the image data sets on each other having optionally to be carried out beforehand.

Alternatively, the chronologically spaced risk parameter values are compared with one another on a result level. In other words, follow-up examinations with the aid of which the risk parameter values can be determined more precisely. This means that a more precise prediction can be made for the future development of the plaque. Likewise the chronological development can serve as an indicator for a therapy response, in order to therefore confirm or refute the success of the therapy. Moreover, in the context of this follow-up examination, a check can be carried out whether and to what extent the risk parameter values for previous examinations were determined correctly. The results of this check can advantageously serve as a reference for a machine-learning process, which is described later in even more detail.

For a method according to at least one embodiment of the invention, projection data sets have preferably been acquired beforehand in a high resolution mode, in particular using a CT device with a photon-counting detector. Photon-counting detectors are designed for example, as directly converting semiconductor detectors that determine the X-rays in an energy-resolved manner. The high resolution mode (HRCT) basically denotes modes of acquisition in which the resolution is maximized. This can be achieved, for example, by oversampling (low pitch, spring focus on the detector or such like) and/or by optimizing the geometry of the CT device (narrow focus, reducing of the detector aperture by UHR-comb or such like). This avoids uncertainties in characterization, such as those that occur for example, due to "calcium blooming".

In the method according to at least one embodiment of the invention, the acquisition of the character parameter values and/or the acquisition of the risk parameter values preferably includes a machine-learning process, particularly preferably based on a database of reference examination subjects. In the context of the machine-learning process, criteria are determined that additionally improve the acquisition of the character parameter values and/or the acquisition of the risk parameter values. This involves in particular complex criteria, with the aid of which a computation unit or a computer for example, can analyze on the basis of an algorithm how plaque can be better characterized using the spectrally different image data sets and how the informative value of the risk parameter can be further increased.

A preferable learning process includes the following steps: first learning data, particularly preferably from the database of reference examination subjects, is acquired. The learning data is image data that has been acquired with different X-ray energies. By way of the learning data, a plurality of plaques are subsequently characterized and in addition, particularly preferably, risk parameter values are also subsequently determined with the aid of the method according to the invention—optionally, after an image reconstruction from the raw data. The results obtained therefrom are monitored or evaluated in a further step. The evaluation can ensue through an operator, for example, using a grading scale. The evaluation can also be carried out, however, on the basis of follow-up examinations, wherein the character parameter values that were determined beforehand and/or the risk parameter values can be checked for their statistical significance, taking into account the plaque development.

In the method according to at least one embodiment of the invention, in an additional step the character parameter values and/or risk parameter values can preferably be locally assigned, and particularly preferably displayed. Here the parameter values will quite particularly preferably be output locally as a figure—that is, assigned to a spatially corresponding pixel. They can be displayed for example, in the position of a mouse cursor or as mean value for a region of interest (ROI).

Alternatively or additionally, a superimposed image, which is based on an image data set and in which the parameter values are displayed in graphically encoded form, is quite particularly preferably output. This means that for example, a slice image from the low energy image data set (or from the high energy image data set) is shown in grayscale values. In addition, the character parameter values are visualized on a pixel by pixel basis in different color shades, for example, red, and the risk parameter values in different color shades, for example, green. In such a representation, it is easy for an operator to determine which categories of plaque are arranged in which positions in the blood vessel and how high the risk of a plaque rupture locally is to be estimated.

The output can alternatively or additionally also be achieved in a storage device that is connected either directly or via a network, in which it is stored and from which it can be downloaded at a later point in time.

The method according to at least one embodiment of the invention can also include segmentation. The segmentation can be achieved automatically, for example, by way of known segmentation methods or manually by an operator. In the context of the segmentation, the image data sets are divided into regions, in which for example, there is first iodine contrasted blood, second vascular walls or connective tissue, and third accumulation of plaque. The further steps of the method can then be used advantageously on those segments that are located inside the vascular walls, but do not contain any contrasted blood.

Preferably, the region of interest (ROI), on which the method according to the invention is used, can be established beforehand automatically or by an operator. This is advantageously resource-saving since for example, the necessary acquisition steps have to be applied not to the entire region captured by the image data, but just only to the regions of interest.

The CT device in a computed tomography system according to at least one embodiment of the invention is a multi-energy CT device. A multi-energy CT device is understood here as a dual-source CT device, a CT device with kV-switching (slow or fast), a CT device with pre-filtering of the tube spectrum, a CT device with multi-layer detector and/or a CT device with an energy-selective photon-counting detector or such like.

Particularly preferably, the CT device is designed for an ECG-triggered or an ECG-gated acquisition of the projection data. As a result thereof, examinations of moving vessels are advantageously also possible, such as for example, of the coronaries.

FIG. 1 shows by way of example and in rough diagram form a computed tomography system 1 according to an embodiment of the invention, which includes a user terminal 20 and a computed tomography device 2. The computed tomography system 1 is designed to carry out the method according to the invention for the characterization of plaque. The computed tomography device 2 includes a patient table 12 for positioning a patient 10 as an examination subject, which table can be moved along a system axis 6. The system axis 6 is referred to hereinafter as the z-axis, which can be moved with the patient 10 into the measurement field.

The device further includes a gantry 3 comprising a source-detector-arrangement 4, 5, which is rotatably positioned around the system axis 6. The source-detector-arrangement 4, 5 comprises an X-ray source 5 and a quanta-counting detector 4, which are aligned facing one another such that when in operation, X-rays emitted from the focus of the X-ray source 5 impinge on the detector 4.

The X-ray source is designed for rapid kV-switching. This means that, during a scan, it changes its tube voltage between 80 kV and 140 kV at a frequency of, for example, 1000 Hz.

The detector 4 is structured for spatially resolved detection of X-rays in individual pixels 7, which are arranged in a plurality of detector lines. Currently, detectors 4 that have a total of 64 or more lines and a spatial resolution in the submillimeter range are being used. For each projection, the detector 4 generates a set of projection data. Here the projection data represent the attenuation values for all the pixels 7 in the X-rays attenuated by the patient 10. They are acquired in separate bins for the pixels 7 from the detector, 4 according to their energy level.

Such a computed tomography device 2 is known to be used for 3D image reconstruction. To acquire an image of a region of interest, projection data are acquired from a plurality of different projection directions as the source-detector arrangement 4, 5 rotates. In the event of a spiral scan, a continual adjustment of the patient table 12 in the direction of the system axis 6 ensues at the same time during a rotation of the source-detector arrangement 4, 5, for example. In this type of scan, the X-ray source 5 and the detector 4 consequently move on a helical trajectory around the patient 10.

The computed tomography system 1 additionally includes a user terminal 20 with an image reconstruction apparatus 24 of an analytical device 25, a display unit 21, for example, a monitor, and an input unit 22, for example, a keyboard, to record user inputs. The analytical device 25 is designed to carry out the method according to the invention. The projection data that have been acquired are first reconstructed using a known method and then by way of the method according to the invention converted into a resulting superimposed image, which for example, can be shown on the display unit 21 and/or which can be stored in a memory in and/or forwarded to other systems. The detailed design of the analytical device 25 is described hereinafter with reference to FIG. 2.

FIG. 3 shows by way of example a block circuit diagram of an analytical device 25 according to the invention. It includes an image data interface 30, an acquisition unit 32, a characterization unit 33, an evaluation unit 34, a visualization unit 37, and an output interface 38, which are connected via a bus 31 to the data transmission system. Data can thus be freely exchanged between the components of the analytical device 25 via the bus 31. The analytical device 25 further includes a morphology data interface 35 and a flow data interface 36, which are connected to the evaluation unit 34.

The analytical device 25 is connected via the interfaces 30, 35, 36, 38 to a network, for example, memory units and/or other components of the CT system 1, such as the reconstruction unit 14. They are used for data transmission from the analytical device 25 to these components and where necessary, vice versa.

FIG. 3 shows in block diagram form a simple example embodiment of a method according to the invention with three steps, which is carried out with the aid of the analytical device 25 that is described in FIG. 2. In a first step I, two image data sets $BD_{HE}$, $BD_{LE}$ are acquired via the image data interface 30. The image data sets $BD_{LE}$, $BD_{HE}$ have been detected initially using the CT device 2 in a preparatory acquisition step that is not part of the method according to the invention as projection data sets with different X-ray energy spectra (80 kV for the low energy image data set $BD_{LE}$ and 140 kV for the high energy image data set $BD_{HE}$). They have subsequently been reconstructed into a low energy image data set $BD_{LE}$ and a high energy image data set $BD_{HE}$. The image data sets $BD_{LE}$, $BD_{HE}$ are optionally registered one over the other in order to allow a uniform data positioning.

In a second step II, a dual energy ratio SP1 is calculated in the acquisition unit 32 in each case as a spectral parameter value from the image data sets $BD_{LE}$, $BD_{HE}$ on a pixel by pixel basis, that is, from the respective pixel values voxel by voxel or pixel by pixel. The dual energy ratio SP1 is calculated in each pixel through the quotient $BD_{LE}/BD_{HE}$ from the pixel value from the low energy image data set $BD_{LE}$ and the corresponding pixel value from the high energy image data set $BD_{HE}$.

In a third step III, in the characterization unit 33, each pixel is assigned to a plaque category according to its calculated dual energy ratio SP1, that is, lipid at values lower than 1 (<1), fibrous at values around 1 (~1) and calcified at values greater than 1 (>1). The respective plaque category corresponds with the character parameter value CP. It can subsequently be forwarded via the output interface 38 to other components of the CT system 1 and thus be displayed with the aid of the display unit 21, for example.

FIG. 4 shows a block diagrammatic representation of a further embodiment of a method according to the invention. Steps I and II are carried out by analogy with the method illustrated by FIG. 3. In a step II', values for the dual energy index SP2 are likewise calculated in the acquisition unit 32, pixel by pixel on the basis of the image data sets $BD_{LE}$, $BD_{HE}$ as values of a second spectral parameter by way of the following formula:

$$\frac{BD_{80}(x) - BD_{140}(x)}{BD_{80}(x) + BD_{140}(x) + 2000}$$

wherein $BD_{80}(x)$ denotes a pixel value for the pixel x in the low energy image data set $BD_{LE}$ and $BD_{140}(x)$ denotes a pixel value for the pixel x in the high energy image data set $BD_{HE}$. Here, the scaling factor α has been set at 2000.

In a third step III', which is a modification thereof, character parameter values CP are determined in the characterization unit 33 from the values for the dual energy ratio SP1 and the dual energy index SP2. This is achieved on a pixel by pixel basis by way of a weighted addition, in which a weighting coefficient is selected as required.

In a fourth step IV, flow data FD, which has been acquired beforehand with the aid of a CT-FFR scan, is obtained with the aid of the flow data interface 36. Here, the flow data FD includes, for example, an entire flow profile within a vessel or a pressure difference that is prevalent between two positions in front of or behind the plaque.

Moreover, in a fifth step V, morphological data MD, which has been acquired beforehand from a structural analysis of the image data sets $BD_{LE}$, $BD_{HE}$, for example, is obtained via the morphology data interface 35. The morphological data MD includes, for example, a length, a volume and/or a parameter relating to the form of plaque. Optionally, by way of the morphological data MD, a "positive remodeling", that is, a reactive commercial remodeling process in response to the increased physiological or pathological stress, is detected in the vessel.

In a sixth step VI, risk parameter values RP are acquired on a pixel by pixel basis in the evaluation unit 34. For this purpose, a simulation can be carried out, for example. This incorporates, for example, the shear forces acting on the plaque, which result from local flows included in the flow data FD. Secondly, the form of plaque, based on the morphological data MD, and the composition thereof, based on the character parameter values CP, are taken into account. Alternatively, the risk parameter values RP can also be determined using complex criteria which have been set beforehand in the context of a machine-learning process.

In a seventh step VII, a diagram is produced in the visualization unit 37, that is, an image to be output, for display on the display unit 21. The diagram can basically also incorporate all the data used hitherto, FD, MD, or the values SP1, SP2, CP, RP, such that a selection can be made by a user as to which elements are to be displayed. The diagram can, for example, be based on one of the image data sets $BD_{LE}$, $BD_{HE}$, that is, used in the background as grayscale tones. The flow data FD can be shown symbolically as a vector field, by way of vectors. The parameter values can for example, be superimposed in color (for example, the risk parameter values RP in red and the character parameter values CP in green) in shades that correspond with the amount thereof, as an overlay for the background. This graphically encoded diagram can be adjusted interactively by a user via an input via the input unit 22 and is finally transmitted as diagram data DD to the display unit 21 and displayed thereon.

FIG. 5 shows four diagrammatic cross-section views through a blood vessel of a patient that illustrate different steps in a method according to the invention. Blood is flowing through the vessel shown in a flow direction FR.

In an abstracted image of matter MB, which represents the actual arrangement of the matter that is prevalent in the vessel, the vessel is mainly filled with blood B.0. On one edge of the vessel, different types of plaque LP.0, FP.0 and CP.0 have accumulated on a vascular wall. In the matter image MB, a clear distinction can be made between lipid plaque LP.0, fibrous plaque FP.0 and calcified plaque CP.0.

Views $BD_{LE}$, $BD_{HE}$ represent slice images from the low energy image data set $BD_{LE}$ and the high energy image data set $BD_{HE}$. All the components in the matter arrangement B.1, LP.1, FP.1 and CP.1 and B.2, LP.2, FP.2 and CP.2 are reproduced in grayscale, which renders a characterization of the plaque more difficult. In particular, the fibrous plaque FP.1 and the calcified plaque CP.1 can hardly be differentiated between in the high energy image data set $BD_{HE}$.

In contrast, in the view according to an embodiment of the invention, which is based on the dual energy index SP2, all the components B.3, LP.3, FP.3 and CP.3 can be clearly differentiated. In particular, the different types of plaque deposits LP.3, FP.3 and CP.3 can be clearly visibly divided here into lipid plaque LP.3, fibrous plaque FP.3, and calcified plaque CP.3 due to the clear color diagram, which makes diagnosis and/or prognosis or risk evaluation far easier.

In conclusion, it is once again pointed out that the apparatus and methods that have been described in detail are only embodiments, which can be modified in various ways by a person skilled in the art, without going beyond the scope of the invention. Furthermore, the use of the indefinite article "a" or "an" does not preclude the relevant features from also being present in plurality. Likewise, the terms "unit", "apparatus", "device", and "system" do not preclude the relevant component from consisting of a plurality of partial components that work in combination and which can optionally also be spatially distributed. Conversely, however, for example, the interfaces of the analytical device can also be combined in a common interface.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for characterization of plaque in a region of interest inside a vessel, used to transport blood, of an examination subject by way of at least a first image data set and a second image data set, the first image data set including a plurality of pixels and being reconstructed from a first projection data set acquired via a CT-device using a first X-ray energy spectra, and the second image data set including the plurality of pixels and being reconstructed from a second projection data set acquired via the CT-device using a second X-ray energy spectra, the method comprising:
- acquiring the first image data set and the second image data set;
- acquiring, on a pixel by pixel basis, spectral parameter values using at least the first image data set and the second image data set, the spectral parameter values for a respective pixel, among the plurality of pixels, including a dual energy index; and
- acquiring, on a pixel by pixel basis, character parameter values, which characterize the plaque in the region of interest inside the vessel of the examination subject, based on the spectral parameter values; wherein
  - the first X-ray energy spectra is different from the second X-ray energy spectra, and
  - the dual energy index for the respective pixel is based on a difference between a first pixel value for the respective pixel in the first image data set and a second pixel value for the respective pixel in the second image data set divided by a sum of the first pixel value, the second pixel value and a scaling factor.

2. The method of claim 1, further comprising:
determining risk parameter values from the character parameter values.

3. The method of claim 2, wherein the determining of the risk parameter values includes using, in addition to the character parameter values, at least one of morphological data, a chronological evolution of the character parameter values and the morphological data, or blood flow data.

4. The method of claim 3, wherein the determining of the risk parameter values includes using, in addition to the character parameter values, blood flow data of blood within the vessel.

5. The method of claim 2, wherein at least one of the acquiring of the character parameter values or the determining of the risk parameter values includes a machine learning process.

6. The method of claim 5, wherein the machine learning process is based on a database of reference examination subjects.

7. The method of claim 2, further comprising:
locally assigned outputting of at least one of the character parameter values or the risk parameter values, wherein
  the at least one of the character parameter values or the risk parameter values are at least one of output as a figure that is locally assigned or output in graphically encoded form in a superimposed image that is based on one of the first image data set or the second image data set.

8. The method of claim 1, further comprising:
determining risk parameter values from the character parameter values and using blood flow data of blood within the vessel.

9. The method of claim 1, further comprising:
determining risk parameter values from the character parameter values and using a chronological evolution of the character parameter values and morphological data.

10. The method of claim 1, wherein the first projection data set and the second projection data set are acquired using a CT device with a photon-counting detector.

11. The method of claim 1, wherein the acquiring of the character parameter values includes a machine learning process.

12. The method of claim 11, wherein the machine learning process is based on a database of reference examination subjects.

13. The method of claim 1, further comprising:
locally assigned outputting of the character parameter values, wherein
  the character parameter values are at least one of output as a figure that is locally assigned or output in graphically encoded form in a superimposed image that is based on one of the first image data set or the second image data set.

14. The method of claim 1, further comprising:
determining risk parameter values from the character parameter values and using at least one of blood flow data of blood within the vessel or a chronological evolution of the character parameter values and morphological data.

15. The method of claim 1, wherein the acquiring of the character parameter values is based on attenuation data and the spectral parameter values.

16. An analytical device for characterization of plaque in a region of interest inside a vessel, used to transport blood, of an examination subject, the analytical device comprising:
- an image data interface to acquire at least a first image data set and a second image data set, the first image data set including a plurality of pixels and being reconstructed from a first projection data set acquired via a CT device using a first X-ray energy spectra, and the second image data set including the plurality of pixels and being reconstructed from a second projection data set acquired via the CT device using a second X-ray energy spectra;
- an acquisition unit to acquire, on a pixel by pixel basis, spectral parameter values using at least the first image data set and the second image data set, the spectral parameter values for a respective pixel, among the plurality of pixels, including a dual energy index; and
- a characterization unit to acquire, on a pixel by pixel basis, character parameter values, which characterize the plaque in the region of interest inside the vessel of the examination subject, from the spectral parameter values; wherein
  - the first X-ray energy spectra is different from the second X-ray energy spectra, and
  - the dual energy index for the respective pixel is based on a difference between a first pixel value for the respective pixel in the first image data set and a second pixel value for the respective pixel in the second image data set divided by a sum of the first pixel value, the second pixel value and a scaling factor.

17. A computed tomography system, comprising:
a CT device; and
the analytical device of claim 16.

18. The computed tomography system of claim 17, wherein the CT device is designed as a multi-energy CT device.

19. A non-transitory computer program product, including a computer program directly loadable into a memory unit of an analytical device, the computer program including program segments to carry out the method of claim 1 when the computer program is run in the analytical device.

20. A non-transitory computer-readable medium, storing program segments, readable and executable by a computation unit, to carry out the method of claim 1 when the program segments are run by the computation unit.

21. A non-transitory computer program product, including a computer program directly loadable into a memory unit of an analytical device, the computer program including program segments to carry out the method of claim 2 when the computer program is run in the analytical device.

22. A non-transitory computer-readable medium, storing program segments, readable and executable by a computation unit, to carry out the method of claim 2 when the program segments are run by the computation unit.

23. An analytical device for characterization of plaque in a region of interest inside a vessel, used to transport blood, of an examination subject, the analytical device comprising:
   an image data interface to acquire at least a first image data set and a second image data set, the first image data set including a plurality of pixels and being reconstructed from a first projection data set acquired via a CT device using a first X-ray energy spectra, and the second image data set including the plurality of pixels and being reconstructed from a second projection data set acquired via the CT device using a second X-ray energy spectra;
   a memory storing computer-readable instructions; and
   one or more processors configured to execute the computer-readable instructions such that the one or more processors are configured to
      acquire, on a pixel by pixel basis, spectral parameter values using at least the first image data set and the second image data set, the spectral parameter values for a respective pixel, among the plurality of pixels, including a dual energy index, and
      acquire, on a pixel by pixel basis, character parameter values, which characterize the plaque in the region of interest inside the vessel of the examination subject, from the spectral parameter values; wherein
         the first X-ray energy spectra is different from the second X-ray energy spectra, and
         the dual energy index for the respective pixel is based on a difference between a first pixel value for the respective pixel in the first image data set and a second pixel value for the respective pixel in the second image data set divided by a sum of the first pixel value, the second pixel value and a scaling factor.

24. A computed tomography system, comprising:
   a CT device; and
   the analytical device of claim 23.

25. The computed tomography system of claim 24, wherein the CT device is designed as a multi-energy CT device.

26. A method for characterization of plaque in a region of interest inside a vessel, used to transport blood, of an examination subject by way of a plurality of image data sets, reconstructed from a plurality of projection data sets respectively acquired via a CT-device using different respective X-ray energy spectra, the method comprising:
   acquiring the plurality of image data sets, each of the plurality of image data sets including a plurality of pixels;
   acquiring, on a pixel by pixel basis, spectral parameter values using at least two of the plurality of image data sets, the spectral parameter values for each pixel including at least one of (i) a dual energy index or (ii) a combination of a dual energy ratio and the dual energy index; and
   computing, on a pixel by pixel basis, character parameter values based on attenuation data and at least one of (i) a comparison between the dual energy index and one or more first threshold values or (ii) a comparison between the combination of the dual energy ratio and the dual energy index and one or more second threshold values, wherein
      the character parameter values characterize the plaque in the region of interest inside the vessel of the examination subject, and
      the dual energy index for the respective pixel is based on a difference between a first pixel value for the respective pixel in a first of the at least two of the plurality of image data sets and a second pixel value for the respective pixel in a second of the at least two of the plurality of image data sets, divided by a sum of the first pixel value, the second pixel value and a scaling factor.

\* \* \* \* \*